(12) United States Patent
Aramata et al.

(10) Patent No.: US 7,420,075 B2
(45) Date of Patent: Sep. 2, 2008

(54) PREPARATION OF ORGANOHALOSILANES

(75) Inventors: Mikio Aramata, Gunma-ken (JP); Hajime Ishizaka, Annaka (JP); Tetsuya Inukai, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 513 days.

(21) Appl. No.: 10/919,072

(22) Filed: Aug. 16, 2004

(65) Prior Publication Data

US 2005/0043557 A1  Feb. 24, 2005

(30) Foreign Application Priority Data

Aug. 21, 2003  (JP) ............... 2003-297246
Jun. 17, 2004  (JP) ............... 2004-179538

(51) Int. Cl.
*C07F 7/16* (2006.01)

(52) U.S. Cl. .................................. 556/472

(58) Field of Classification Search ............ None
See application file for complete search history.

(56) References Cited

U.S. PATENT DOCUMENTS

| | | | |
|---|---|---|---|
| 2,380,995 A | 8/1945 | Rochow et al. | |
| 4,500,724 A | 2/1985 | Ward, III et al. | |
| 6,156,380 A * | 12/2000 | Aramata et al. | 427/217 |
| 6,288,258 B1 * | 9/2001 | Aramata et al. | 556/472 |
| 6,395,917 B1 * | 5/2002 | Ishizaka et al. | 556/472 |
| 6,894,181 B2 * | 5/2005 | Ueno et al. | 556/472 |
| 7,179,933 B2 * | 2/2007 | Inukai et al. | 556/472 |
| 2002/0156310 A1 | 10/2002 | Inukai et al. | |
| 2005/0209474 A1 * | 9/2005 | Inukai et al. | 556/472 |
| 2006/0084821 A1 * | 4/2006 | Aramata et al. | 556/472 |

FOREIGN PATENT DOCUMENTS

| | | |
|---|---|---|
| JP | 32-4570 B | 7/1957 |
| JP | 33-1370 B | 2/1958 |
| JP | 1-40035 B2 | 8/1989 |

OTHER PUBLICATIONS

E.G. Rochow et al, The Direct Synthesis of Phenylchlorosilanes, XP-002306098, Journal of the American Chemical Society, vol. 67, pp. 1772-1774 (1945).

Eugene G. Rochow, J. Am. Chem. Soc. The direct Synthesis of Organosilicon Compounds, vol. 67, Jun. 1945, pp. 963-965.

Eugene G. Rochow et al., J. Am. Chem. Soc., The direct Synthesis of Phenylchlorosilanes., vol. 67, Oct. 1945 pp. 1772-1774.

* cited by examiner

*Primary Examiner*—Samuel A Barts
(74) *Attorney, Agent, or Firm*—Birch, Stewart, Kolasch & Birch, LLP (57) ABSTRACT

Organohalosilanes are prepared by charging a reactor with a contact mass of metallic silicon and a catalyst and feeding an organohalide-containing gas to the reactor. Tin or a tin compound is used as the catalyst. Then organohalosilanes can be produced quite efficiently at a high reaction rate while maintaining a low T/D ratio and minimizing the deposition of by-products and carbon.

12 Claims, 3 Drawing Sheets

FIG.1

ROTATING DIRECTION

PREPARATION OF ORGANOHALOSILANES

CROSS-REFERENCE TO RELATED APPLICATION

This Nonprovisional application claims priority under 35 U.S.C. §119(a) on Patent Application Nos. 2003-297246 and 2004-179538 filed in Japan on Aug. 21, 2003 and Jun. 17, 2004, respectively, the entire contents of which are hereby incorporated by reference.

TECHNICAL FIELD

This invention relates to a direct process for preparing organohalosilanes, and more particularly, to a direct process for preparing organohalosilanes, especially phenylchlorosilanes, through gas-solid catalytic reaction using tin or tin compounds as a main catalyst instead of conventional copper catalysts.

BACKGROUND ART

With respect to the synthesis of organohalosilanes, E. G. Rochow first disclosed direct reaction between metallic silicon and organohalide in the presence of a copper catalyst. See U.S. Pat. No. 2,380,995 and J. Am. Chem. Soc., 67, 963 (1945), "The direct synthesis of organosilicon compounds." Further, J. Am. Chem. Soc., 67, 1772 (1945), "The direct synthesis of phenylchlorosilanes" reports that the contact mass is useful in the synthesis of phenylsilanes. After these reports, copper catalysts are acknowledged as prevailing catalysts in the organohalosilane synthesis by direct reaction of metallic silicon with organohalide. Since then, there have been reported a number of research works relating to various co-catalysts used together with copper catalysts, copper catalysts themselves and their treatment, reactors, additives used during reaction, and the like. All prior art investigations relate to copper catalyzed reactions.

On the other hand, tin serves as a catalyst in the contact mass for organohalosilane direct synthesis reaction, but in fact, tin is used solely as a co-catalyst for promoting reaction when copper is used as the main catalyst. For instance, U.S. Pat. No. 4,500,724 and JP-B 1-40035 disclose use of tin for methylhalosilane synthesis, JP-B 33-1370 discloses tin or tin alloys for phenylsilane synthesis, and JP-B 32-4570 discloses tin tetrahalides. No reference has been made to the contact masses in which the copper catalyst is absent or the copper catalyst is present in minor amounts, but not used as the main catalyst.

No substantial problems have arisen as long as the reaction deals with only methylhalosilanes. As silicone resins become diversified, there is an increasing demand for organohalosilanes having other organic groups such as phenyl. Synthesis of such organohalosilanes is carried out, as a matter of course, by direct reaction of metallic silicon with chlorobenzene in the presence of copper catalysts. The reaction with such organohalides having low reactivity suffers from the problems that the reaction temperature must be elevated (to about 400 to 600° C.), large amounts of by-products such as biphenyls and carbon form to complicate post-treatment, and the percent conversion of silicon to silane is very low despite a very large amount of the catalyst used.

SUMMARY OF THE INVENTION

An object of the invention is to provide a direct process for preparing organohalosilanes using a novel contact mass having a high activity and causing minimal side reaction, which contact mass is obtained by using metallic tin or tin compounds as a main catalyst, but not copper or copper compounds which have been considered essential as a main catalyst, and thoroughly premixing the tin with silicon powder.

Addressing a process for direct synthesis of organohalosilanes by reaction of organohalides having low reactivity with metallic silicon, e.g., a process for preparing organohalosilanes by industrially advantageous direct reaction of chlorobenzene with metallic silicon, the inventors have discovered a novel contact mass using tin or a tin compound as a main catalyst. The above and other objects of the invention can be attained by adding tin or a tin compound to metallic silicon powder, preferably in an amount of 0.01 to 50% by weight based on the weight of the silicon powder, intimately mixing them, and using the resulting mixture as a contact mass for the above-described reaction. As compared with the conventional contact mass using copper as the main catalyst, the novel contact mass is effective in maintaining at least equal reactivity, improving the composition of organohalosilanes, especially diorganodihalosilane, and significantly reducing formation of biphenyl and carbonaceous by-products during phenylhalosilane synthesis. As a result, the percent conversion of silicon is drastically increased.

The preparation of phenylchlorosilane is further discussed. Since tin has a relatively low melting point of 232° C., a problem might arise at the temperature for the reaction of metallic silicon with chlorobenzene to synthesize phenylchlorosilane. That is, if an excess amount of tin is used, molten tin will deposit on the bottom of the reactor, which means that all the tin added does not exert effective catalysis. Unexpectedly, the use of metallic silicon particles having fines of tin and/or tin compound dispersed and deposited thereon can find a compromise between very high productivity and minimized formation of biphenyls and benzenes in the preparation of phenylchlorosilane by direct reaction. In the reaction to synthesize phenylchlorosilane by bringing chlorobenzene in contact with a contact mass consisting essentially of metallic silicon and a tin-based catalyst, the tin added develops its catalysis to a full extent, achieving an improved reactivity.

Accordingly, the present invention provides a process of preparing organohalosilanes having the general formula (1):

$$R_nH_mSiX_{(4-n-m)} \quad (I)$$

wherein R is a monovalent hydrocarbon group, X is a halogen atom, n is an integer of 1 to 3, m is an integer of 0 or 1, and the sum of n+m is 1 to 3, by charging a reactor with a contact mass comprising metallic silicon and a catalyst and feeding an organohalide-containing gas to the reactor, wherein tin or a tin compound is used as the main catalyst.

The tin catalyst (tin or tin compound) is preferably in the form of metallic tin, tin alloy, tin oxide or tin halide and added in an amount to provide 0.01 to 50% by weight of metallic tin based on the weight of metallic silicon.

Also preferably, metallic silicon and the tin or tin compound are previously mixed under substantial shear forces or heat treated to form a precursor, which is fed to the reactor. More preferably, metallic silicon particles and the tin or tin compound are rubbed together by mechanically applying high shear forces in a non-oxidizing atmosphere, for dispersing and depositing the tin or tin compound onto surfaces of metallic silicon particles, which are fed to the reactor. The means for mechanically applying high shear forces may be a mechanofusion device, ball mill, media agitating mill, planetary mill, high-speed tumbling mill, jet mill, shearing mill or roller mill. Preferably the non-oxidizing atmosphere may comprise nitrogen, argon, hydrogen or a mixture thereof.

In the process of the invention, the organohalide is typically phenyl chloride whereby phenylchlorosilanes are prepared.

In the preparation of organohalosilanes at a high reaction rate, the organohalosilanes can be produced quite efficiently while maintaining a low T/D ratio and minimizing the deposition of by-products and carbon. Here T represents organotrihalosilane and D represents diorganodihalosilane, and a low T/D means a good selectivity of useful organohalosilane.

The invention permits the tin or tin compound added to develop its catalysis to a full extent and thus enables preparation of phenylchlorosilanes with the advantages of a high productivity and minimized by-product formation.

DESCRIPTION OF THE PREFERRED EMBODIMENTS

According to the process of the invention, organohalosilanes are prepared by direct reaction of metallic silicon with an organohalide, and more particularly, by charging a reactor with a contact mass which is a premix of metallic silicon and a tin catalyst, instead of a conventional contact mass of metallic silicon and a copper catalyst, and feeding an organohalide-containing gas to the reactor.

The metallic silicon used herein preferably has a silicon purity of at least 97% by weight, especially at least 98% by weight. Prior to use, the metallic silicon is preferably ground into particles with an appropriate particle size. Where the reactor used is a fluidized bed or stirred bed reactor, the metallic silicon powder should preferably have a particle size in the range of 10 to 100 µm, corresponding to 50% of the weight-base cumulative size distribution curve on sieving.

The tin catalysts used herein include metallic tin and tin alloys such as tin-zinc alloys in granular or flake powder form, and various forms of tin compounds such as tin oxides and tin halides. In the tin compounds, tin may be divalent or tetravalent.

The powdered metallic tin and tin alloys are commercially available. For example, a tin foil powder from Toyo Metal Powder Co., Ltd. is useful.

The metallic tin and tin compound powders should preferably have an average particle size in the range of 1 to 200 µm, more preferably 1 to 75 µm, even more preferably 1 to 50 µm, further more preferably 1 to 30 µm, corresponding to 50% of the weight-base cumulative size distribution curve on sieving. With too small an average particle size, only a few tin particles may attach to surfaces of metallic silicon particles and many tin particles may scatter out of the reactor during activation, failing to exert the desired effect. Tin particles with too large an average particle size will settle down to the bottom of the contact mass, detracting from dispersity.

An appropriate amount of the tin catalyst added is 0.01 to 50 parts by weight, more preferably 1 to 15 parts by weight, even more preferably 1 to 8 parts by weight, calculated as metallic tin, per 100 parts by weight of metallic silicon. Too small an amount of the tin catalyst may fail to achieve the desired effect to a full extent whereas too large an amount may allow tin to precipitate as liquid in the reaction system, incurring disordered flow or poor contact.

In a preferred embodiment of the invention, metallic silicon and the tin or tin compound are previously mixed under substantial shear forces or heat treated to form a precursor, which is fed to the reactor. This may be done by braying in a mortar. In a preferred industrial practice, metallic silicon and the tin or tin compound are rubbed together by mechanically applying high shear forces in a non-oxidizing atmosphere.

Such a precursor-forming method enables the tin added to effectively serve as the catalyst, thus significantly accelerating the progress of phenylchlorosilane synthesis reaction.

When metallic silicon particles and tin or tin compound particles are rubbed together by mechanically applying high shear forces as mentioned above, the tin or tin compound is dispersed and deposited onto surfaces of metallic silicon particles. Specifically, the tin or tin compound is deposited on surfaces of metallic silicon particles in the state that fractured particles, flake particles, hemispherical or hemi-ellipsoidal particles or otherwise shaped particles of the tin or tin compound are dispersed as groups of islands or a plurality of discrete islands. The tin or tin compound deposits or islands preferably have a thickness or height of up to 20 µm, more preferably up to 15 µm, as observed under a microscope. The contact mass of metallic silicon and tin and/or tin compound combined in this way is used in the synthesis of phenylchlorosilanes by direct reaction, thereby achieving a very high productivity without substantially increasing the formation of benzene and biphenyl by-products.

It is now described how to attach or deposit tin and/or tin compound particles to surfaces of metallic silicon particles although the smearing method is not limited thereto.

A typical method of attaching tin and/or tin compound particles to surfaces of metallic silicon particles is by mechanically applying high shear forces to metallic silicon and tin and/or tin compound in a non-oxidizing atmosphere for rubbing them together.

Figure 1:
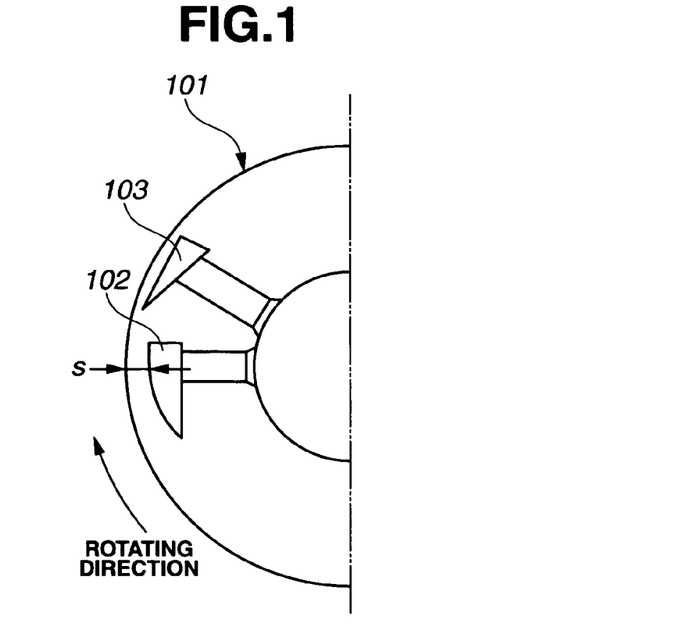
FIG. 1 schematically illustrates a mechanofusion device.

Referring to FIG. 1, there is schematically illustrated a mechanofusion device which is commercially available, for example, as Model AM-15F by Hosokawa Micron Co., Ltd. The device includes a rotating casing 101 and a stationary support having inner pieces 102 and scrapers 103 mounted thereon (only one set of an inner piece and a scraper is shown). The scraper 103 is located downstream of the inner piece 102 with respect to the rotating direction of the casing 101. Raw material (metallic silicon and tin and/or tin compound) is admitted into the casing 101. The casing 101 is rotated to centrifugally push the raw material against the inner wall of the casing 101 and shear forces are applied to the raw material between the inner piece 102 and the casing 101 whereby the tin and/or tin compound particles are smeared and attached to surfaces of metallic silicon particles. The raw material modified between the casing 101 inner wall and the inner piece 102 is scraped off by the scraper 103. In this way, the operation of applying shear forces to the raw material is repeated. Namely, the mechanofusion device has the rotating casing 101 and the stationary inner piece 102 which cooperate to apply compression, shear and grinding actions to powder particles. The scraper 103 serves to scrape off the powder compressed between the inner piece 102 and the casing 101. The device is capable of applying mechanical energy to particles of a single material or plural materials to achieve (i) surface fusion, (ii) dispersion and mixing, and (iii) particle size control. It is understood that the shear force can be adjusted by controlling the revolution of a motor for driving the casing and the clearance between the casing and the inner piece.

The number of revolutions of the casing 101 and the clearance "s" between the casing 101 and the inner piece 102 are properly selected in accordance with a particular device used. It is preferred for the AM-15F mechanofusion device that the casing 101 be rotated at 300 to 3,000 rpm, and especially 800 to 2,200 rpm, and the clearance be set at 0.1 to 10 mm, and especially 0.5 to 5 mm.

The rubbing operation should preferably be carried out in a non-oxidizing atmosphere, such as nitrogen gas, argon gas, hydrogen gas or a mixture thereof.

In addition to the mechanofusion device, a ball mill, a media agitating mill, a planetary mill, a high-speed tumbling mill, a jet mill, a shearing mill or a roller mill may also be used for smearing or attaching tin or tin compound to surfaces of metallic silicon particles.

To the reaction system, promoters such as zinc, antimony, arsenic and phosphor and compounds and alloys thereof which are used as the co-catalyst in the current silane synthesis reaction, and agents for improving the selectivity of organotrihalosilane, such as iron, aluminum, and halides thereof may be added, and even trichlorosilane may be added as well. It is not critical whether or not these agents are added. It is not necessarily needed to add copper and alloys and compounds thereof. An appropriate amount of these co-catalysts added is 0 to 20 parts by weight, more preferably 0.05 to 5 parts by weight, calculated as the total of co-catalyst metals, per 100 parts by weight of metallic silicon, but should be smaller than the amount of tin added as the tin catalyst.

No copper is essentially used. It is acceptable that copper be included as an incidental impurity in metallic silicon and the catalyst, specifically in an amount of less than 0.1% by weight, especially up to about 0.05% by weight of copper based on the metallic silicon. In phenylhalosilane synthesis, the amount of copper is limited to less than 0.1% based on metallic silicon because biphenyls are likely to form in the presence of 0.1% by weight or more of copper.

The organohalide to be reacted with metallic silicon to form organohalosilanes of the formula (1) typically has the general formula (2).

$$RX \quad (2)$$

Herein, R is a monovalent hydrocarbon group. Suitable monovalent hydrocarbon groups are those of 1 to 12 carbon atoms, for example, aryl groups such as phenyl and tolyl, aralkyl groups such as benzyl, phenylethyl and phenylpropyl, alkenyl groups such as vinyl, allyl, propenyl and butenyl, and alkyl groups such as methyl, ethyl, propyl, butyl and hexyl. X is a halogen atom such as chlorine and bromine. Exemplary organohalides are chlorobenzene, methyl chloride, ethyl chloride, methyl bromide and ethyl bromide. Of these, chlorobenzene and methyl chloride are advantageous in the industry. Chlorobenzene or phenyl chloride is most favorable in the invention.

The organohalide is previously heated and gasified before it is admitted into the reactor. The organohalide vapor or gas may be fed alone or combined with an inert gas. The organohalide gas is fed in a sufficient amount to fluidize the contact mass together with the inert gas, the fluidizing amount being determined as appropriate from the diameter of the reactor and the superficial velocity.

In the step of heating the contact mass or imparting catalytic activity to the contact mass, an inert gas is used for fluidizing the contact mass in the reactor. Such an inert gas may be nitrogen or argon gas, for example, with the nitrogen gas being preferable from the economic standpoint. The flow velocity of the inert gas fed in this and subsequent steps is at least the minimum fluidization velocity of the contact mass, and preferably about 5 times the minimum fluidization velocity. A flow velocity of the inert gas below the range may often fail to achieve uniform fluidization of the contact mass. If the flow velocity of the inert gas is above the range, metallic silicon particles may excessively scatter away with increased losses of the inert gas and heat. It is recommended to recycle the inert gas.

After the contact mass is heated to the reaction temperature or given catalytic activity as mentioned above, the organohalide is introduced into the reactor where gas-solid catalytic reaction takes place between the organohalide and metallic silicon to form organohalosilanes. The conditions for this gas-solid catalytic reaction may be the same as in the conventional Rochow process. For example, the reaction temperature may be in the range of 350 to 500° C.

Figure 2:
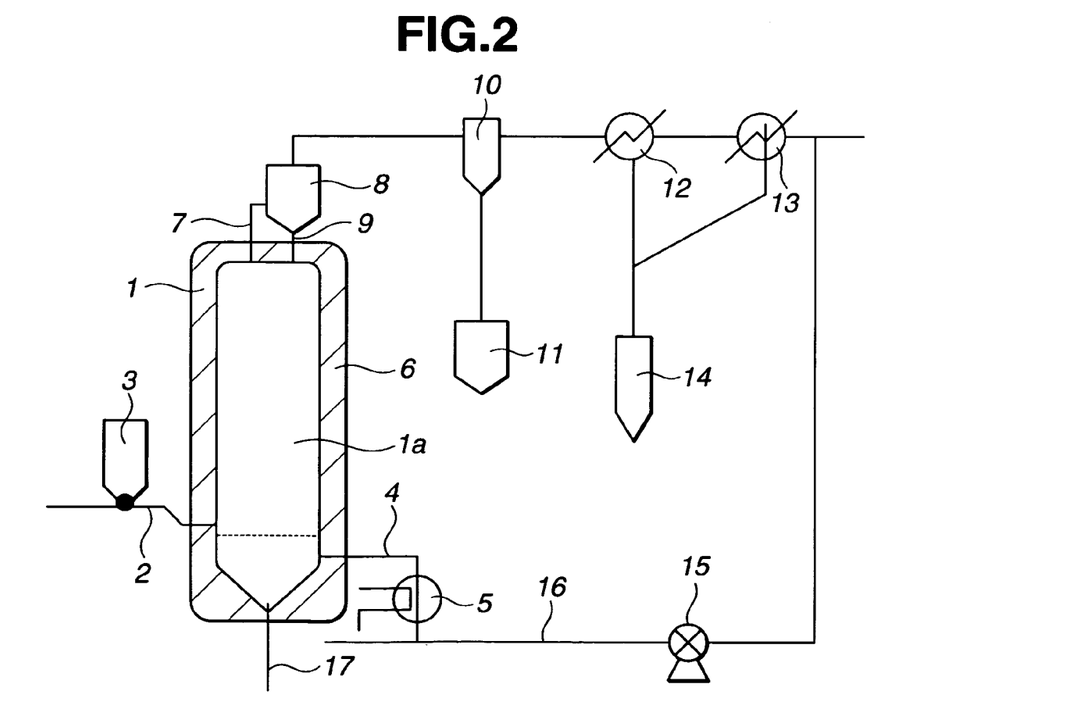
FIG. 2 schematically illustrates a preparation apparatus used in the practice of the invention.

Any desired apparatus may be used for the organohalosilane preparation process of the invention. FIG. 2 illustrates one exemplary preparation apparatus which includes a fluidized bed reactor 1, an input line 2 and a charge feed hopper 3. The hopper 3 contains a contact mass which is prepared by premixing metallic silicon with a tin or tin compound catalyst, optionally in admixture with a co-catalyst. The contact mass is fed to the bottom of the reactor 1 through the line 2. In the contact mass system, tin can precipitate out with the progress of reaction and become liquid or viscous due to combination with silicon, and such liquid or viscous matter is discharged through a discharge line 17. An organohalide feed line 4 surrounded by a heater 5 is also connected to the reactor 1 at the bottom. An organohalide gas or vapor is introduced into the reactor 1 at the bottom for thereby forming a fluidized bed 1a of metallic silicon and catalyst within the reactor 1. The reactor 1 has a cooling jacket 6.

Preferably the organohalide gas or vapor is introduced at a linear velocity of 2 to 20 cm/sec in the steady state. The reaction is typically effected at a temperature of about 350 to 600° C., and especially about 350 to 500° C.

The organohalosilane product resulting from the reaction flows through an output line 7 connected to the top of the reactor 1, and then into a first cyclone 8 where entrained solid particles are separated off. The solid particles are returned to the fluidized bed 1a via a solid particle return line 9. The organohalosilane then passes to a second cyclone 10 where still entrained solid particles are separated off and stored in a separated particle storage tank 11. Next, the organohalosilane is condensed in a first silane condenser or simple evaporator 12, then in a second silane condenser or simple evaporator 13, and is collected and stored in a silane storage tank 14. Some or all of the waste gas and vapor remaining after the solid particles have been separated off and the organohalosilane has been condensed and removed is returned once again to the reactor 1 through an organohalide return line 16 equipped with a circulating pump (circulating gas compressor) 15. The return line 16 is connected to the organohalide feed line 4. A fluidized bed reactor is used in the illustrated embodiment although a stirred bed reactor, a fixed bed reactor or the like may also be used.

The process of the invention is carried out as above to produce organohalosilanes having the general formula (1):

$$R_nH_mSiX_{(4-n-m)} \quad (I)$$

wherein R is a monovalent hydrocarbon group as defined above, X is a halogen atom, n is an integer of 1 to 3, m is an integer of 0 or 1, and the sum of n+m is an integer of 1 to 3. It is preferred from the demand balance that m have an average value of approximately 0 and n have an average value of approximately 1 to 2. Then the product contain a large proportion, typically 50 to 95%, of a diorganodihalosilane (D) (wherein n=2 and m=0) which is most useful as a silicone-forming reactant while the amount of organotrihalosilane (T) (wherein m=0) formed is minimized. Particularly under ideal reaction conditions that avoid contact with a Lewis acid such as ferric chloride, the T/D ratio may be typically up to 0.3, and especially up to 0.1. At the same time, formation of biphenyls as by-products in the reaction of chlorobenzene with metallic silicon is minimized. The amount of such by-products is typically reduced to 1/10 or less, as compared with the conventional reaction processes using copper base catalysts.

EXAMPLE

Examples of the invention are given below by way of illustration and not by way of limitation. All parts and percents are by weight. The average particle size was measured as described above.

Example 1

Figure 3:
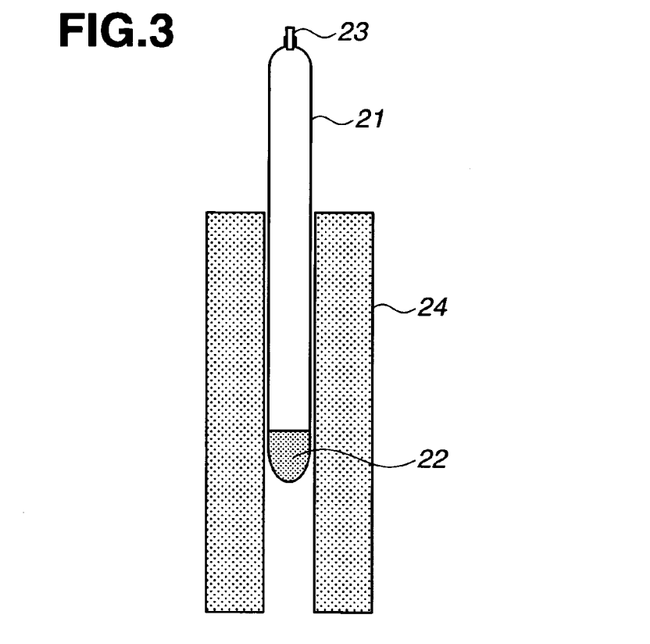
FIG. 3 schematically illustrates an experimental setup used in Examples 1, 2 and 5 and Comparative Examples 1 to 3.

An experiment was carried out using an experimental setup as shown in FIG. 3. A Pyrex® glass tube 21 having an interior volume of 25 ml was furnished. A contact mass was prepared by combining 1.0 g of chemical grade metallic silicon powder having an average particle size of 150 μm with 0.5 g of flaky tin powder having an average particle size of 75 μm and thoroughly mixing in an agate mortar to form a premix. The contact mass 22 (1.5 g) was placed in the tube 21, which was closed with a silicone rubber plug 23. Using a vacuum pump, the tube was evacuated to a vacuum of lower than 0.1 Torr. Through the rubber plug 23, 0.1 ml (0.11 g) of chlorobenzene was injected into the tube. The tube 21 was heated at 450° C. for one hour in a ring furnace 24 and then allowed to cool down. Then 5 ml of chloroform containing 1% methanol (simply referred to as chloroform, hereinafter) was injected, followed by 10 minutes of shaking. The interior was restored to atmospheric pressure. The reaction solution diluted with chloroform was filtered and quantitatively analyzed by gas chromatography. Table 1 shows reaction product species and their quantities.

Example 2

A contact mass which was prepared as in Example 1 by mixing 1.0 g of reagent grade silicon powder having an average particle size of 75 μm with 0.5 g of flaky tin powder having an average particle size of 75 μm in a mortar was placed in a Pyrex® glass tube having an interior volume of 25 ml, which was closed with a plug. The tube was evacuated to a vacuum of lower than 0.1 Torr, after which 0.1 ml (0.11 g) of chlorobenzene was injected. The tube was heated at 450° C. for one hour and then allowed to cool down. Then 5 ml of chloroform was injected, followed by 10 minutes of shaking. The interior was restored to atmospheric pressure. The reaction solution diluted with chloroform was filtered and quantitatively analyzed by gas chromatography. Table 1 shows reaction product species and their quantities.

Comparative Example 1

A Pyrex® glass tube having an interior volume of 25 ml was charged with 1.0 g of reagent grade silicon powder having an average particle size of 75 μm and 0.5 g of flaky copper powder having an average particle size of 75 μm and closed with a plug. The tube was evacuated to a vacuum of lower than 0.1 Torr, after which 0.1 ml (0.11 g) of chlorobenzene was injected. The tube was heated at 450° C. for one hour and then allowed to cool down. Then 5 ml of chloroform was injected, followed by 10 minutes of shaking. The interior was restored to atmospheric pressure. The reaction solution diluted with chloroform was filtered and quantitatively analyzed by gas chromatography. Table 1 shows reaction product species and their quantities.

Comparative Example 2

A Pyrex® glass tube having an interior volume of 25 ml was charged with 1.0 g of chemical grade metallic silicon powder having an average particle size of 150 μm, 0.45 g of flaky copper powder having an average particle size of 75 μm and 0.05 g of flaky tin powder having an average particle size of 75 μm and closed with a plug. The tube was evacuated to a vacuum of lower than 0.1 Torr, after which 0.1 ml (0.11 g) of chlorobenzene was injected. The tube was heated at 450° C. for one hour and then allowed to cool down. Then 5 ml of chloroform was injected, followed by 10 minutes of shaking. The interior was restored to atmospheric pressure. The reaction solution diluted with chloroform was filtered and quantitatively analyzed by gas chromatography. Table 1 shows reaction product species and their quantities.

Comparative Example 3

A Pyrex® glass tube having an interior volume of 25 ml was charged with 1.0 g of chemical grade metallic silicon powder having an average particle size of 150 μm and 0.5 g of flaky copper powder having an average particle size of 30 μm and closed with a plug. The tube was evacuated to a vacuum of lower than 0.1 Torr, after which 0.1 ml (0.11 g) of chlorobenzene was injected. The tube was heated at 450° C. for one hour and then allowed to cool down. Then 5 ml of chloroform was injected, followed by 10 minutes of shaking. The interior was restored to atmospheric pressure. The reaction solution diluted with chloroform was filtered and quantitatively analyzed by gas chromatography. Table 1 shows reaction product species and their quantities.

TABLE 1

|  | Catalyst | Diphenyl-dichlorosilane | Phenyl-trichlorosilane | Biphenyl |
|---|---|---|---|---|
| Example 1 | Sn | 9.72 mg | N.D. | 0.07 mg |
| Example 2 | Sn | 14.62 mg | N.D. | N.D. |
| Comparative Example 1 | Cu | 0.30 mg | 0.05 mg | 1.99 mg |
| Comparative Example 2 | Cu + Sn | 1.30 mg | 8.10 mg | 3.10 mg |
| Comparative Example 3 | Cu | 1.70 mg | 12.74 mg | 1.30 mg |

Example 3

Figure 4:
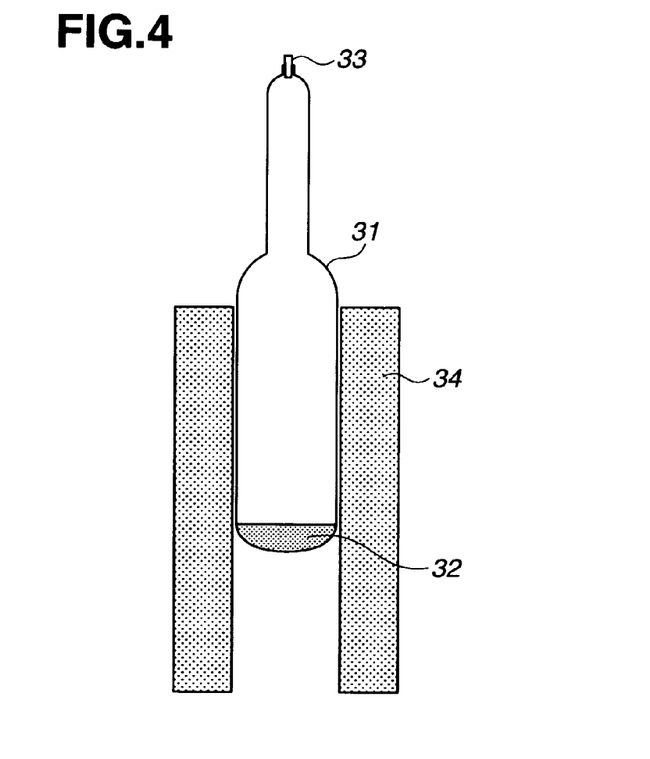
FIG. 4 schematically illustrates an experimental setup used in Example 3 and Comparative Examples 4 to 5.

An experiment was carried out using an experimental setup as shown in FIG. 4. A Pyrex® glass tube 31 having an interior volume of 250 ml was furnished. A contact mass was prepared by combining 10.0 g of chemical grade metallic silicon powder having an average particle size of 150 μm with 5.0 g of flaky tin powder having an average particle size of 75 μm and thoroughly mixing in a mortar. The contact mass 32 was placed in the tube 31, which was closed with a silicone rubber plug 33. The tube was evacuated to a vacuum of lower than 0.1 Torr, after which 10 ml (11 g) of chlorobenzene was injected. The tube 31 was heated at 450° C. for one hour in a ring furnace 34 and then allowed to cool down. Then 50 ml of chloroform was injected, followed by 10 minutes of shaking. The interior was restored to atmospheric pressure. The reaction solution diluted with chloroform was filtered and quantitatively analyzed by gas chromatography. Table 2 shows reaction product species and their quantities.

Comparative Example 4

A Pyrex® glass tube having an interior volume of 250 ml was charged with 10.0 g of chemical grade metallic silicon powder having an average particle size of 150 μm and 5.0 g of flaky copper powder having an average particle size of 75 μm and closed with a silicone rubber plug. The tube was evacuated to a vacuum of lower than 0.1 Torr, after which 10 ml (11 g) of chlorobenzene was injected. The tube was heated at 450° C. for one hour and then allowed to cool down. Then 50 ml of chloroform was injected, followed by 10 minutes of shaking. The interior was restored to atmospheric pressure. The reaction solution diluted with chloroform was filtered and quantitatively analyzed by gas chromatography. Table 2 shows reaction product species and their quantities.

Comparative Example 5

A Pyrex® glass tube having an interior volume of 250 ml was charged with 10.0 g of chemical grade metallic silicon powder having an average particle size of 150 μm, 4.5 g of flaky copper powder having an average particle size of 75 μm and 0.5 g of flaky tin powder having an average particle size of 75 μm and closed with a silicone rubber plug. The tube was evacuated to a vacuum of lower than 0.1 Torr, after which 10 ml (11 g) of chlorobenzene was injected. The tube was heated at 450° C. for one hour and then allowed to cool down. Then 50 ml of chloroform was injected, followed by 10 minutes of shaking. The interior was restored to atmospheric pressure. The reaction solution diluted with chloroform was filtered and quantitatively analyzed by gas chromatography. Table 2 shows reaction product species and their quantities.

TABLE 2

| | Catalyst | Diphenyl-dichlorosilane | Phenyl-trichlorosilane | Biphenyl |
|---|---|---|---|---|
| Example 3 | Sn | 1070 mg | N.D. | 4.0 mg |
| Comparative Example 4 | Cu | 26 mg | 5.0 mg | 170 mg |
| Comparative Example 5 | Cu + Sn | 110 mg | 8.3 mg | 270 mg |

Example 4

100 parts of chemical grade metallic silicon powder having an average particle size of 50 μm and 8 parts of tin powder having an average particle size of 75 μm were mixed such that tin was fully attached to surfaces of metallic silicon particles. The premix was admitted into a fluidized bed reactor equipped with a stirrer, which was heated to a reactor interior temperature of 480° C. Gaseous chlorobenzene was fed into the fluidized bed at a flow velocity of 2 cm/s. The product gas was condensed in a condenser. Table 3 shows the composition of a sample taken at the steady state of reaction.

Comparative Example 6

100 parts of chemical grade metallic silicon powder having an average particle size of 50 μm, 10 parts of copper powder having an average particle size of 75 μm, a catalytic amount (1 part) of zinc powder having an average particle size of 75 μm, and a catalytic amount (0.1 part) of tin powder having an average particle size of 75 μm were admitted into a fluidized bed reactor equipped with a stirrer, which was heated to a reactor interior temperature of 480° C. Gaseous chlorobenzene was fed into the fluidized bed at a flow velocity of 2 cm/s. The product gas was condensed in a condenser. Table 3 shows the composition of a sample taken at the steady state of reaction.

Comparative Example 7

100 parts of chemical grade metallic silicon powder having an average particle size of 50 μm, 6 parts of copper powder having an average particle size of 75 μm, and a catalytic amount (0.1 part) of tin powder having an average particle size of 75 μm were admitted into a fluidized bed reactor equipped with a stirrer, which was heated to a reactor interior temperature of 480° C. Gaseous chlorobenzene was fed into the fluidized bed at a flow velocity of 2 cm/s. The product gas was condensed in a condenser. Table 3 shows the composition of a sample taken at the steady state of reaction.

TABLE 3

| | Catalyst | Diphenyl-dichlorosilane | Phenyl-trichlorosilane | Biphenyl | Unreacted gas |
|---|---|---|---|---|---|
| Example 4 | Sn | 30.6% | 8.0% | 0.2% | balance |
| Comparative Example 6 | Cu + Zn + Sn | 24.0% | 14.7% | 2.1% | balance |
| Comparative Example 7 | Cu + Sn | 6.8% | 7.8% | 1.4% | balance |

Example 5

Deposition of Tin and/or Tin Compound Particles on Surfaces of Metallic Silicon Particles 100 parts of metallic silicon having an average particle size of 50 μm and 8 parts of tin having an average particle size of 75 μm were mixed. Using a mechanofusion device AM-15F (by Hosokawa Micron Co., Ltd.), the mixture was rubbed for one hour in a nitrogen stream under conditions: agitating power 1.5 kW, and casing revolution 1,200 rpm, whereby tin was attached or smeared to surfaces of metallic silicon particles.

An experiment was carried out using an experimental setup as shown in FIG. 3. A Pyrex® glass tube having an interior volume of 25 ml was charged with 1.08 g of the mixture prepared above and closed with a silicone rubber plug. Using a vacuum pump, the tube was evacuated to a vacuum of lower than 0.1 Torr. Through the rubber plug, 0.1 ml (0.11 g) of chlorobenzene was injected into the tube. The tube was heated at 450° C. for one hour in a ring furnace and then allowed to cool down. Then 5 ml of chloroform containing 1% methanol (simply referred to as chloroform, hereinafter)

was injected, followed by 10 minutes of shaking. The interior was restored to atmospheric pressure. The reaction solution diluted with chloroform was filtered and quantitatively analyzed by gas chromatography. Table 4 shows reaction product species and their quantities.

TABLE 4

| | Diphenyl-dichlorosilane | Phenyl-trichlorosilane | Biphenyl | Benzene |
|---|---|---|---|---|
| Example 5 | 7.73 mg | N.D. | 0.10 mg | 1.01 mg |

Example 6

100 parts of metallic silicon having an average particle size of 50 μm and 8 parts of tin having an average particle size of 75 μm were mixed. Using a mechanofusion device AM-15F (by Hosokawa Micron Co., Ltd.), the mixture was rubbed for one hour in a nitrogen stream under conditions: agitating power 1.5 kW, and casing revolution 1,200 rpm, whereby tin was attached or smeared to surfaces of metallic silicon particles.

The mixture prepared above was fed into a fluidized bed reactor equipped with a stirrer through which nitrogen flowed. The reactor was heated to an interior temperature of 480° C. The nitrogen flow was then interrupted, and instead, gaseous chlorobenzene was fed into the fluidized bed at a flow velocity of 2 cm/s. The product gas was condensed in a condenser. Table 5 shows the composition of a sample taken at the steady state of reaction.

Example 7

Figure 5:
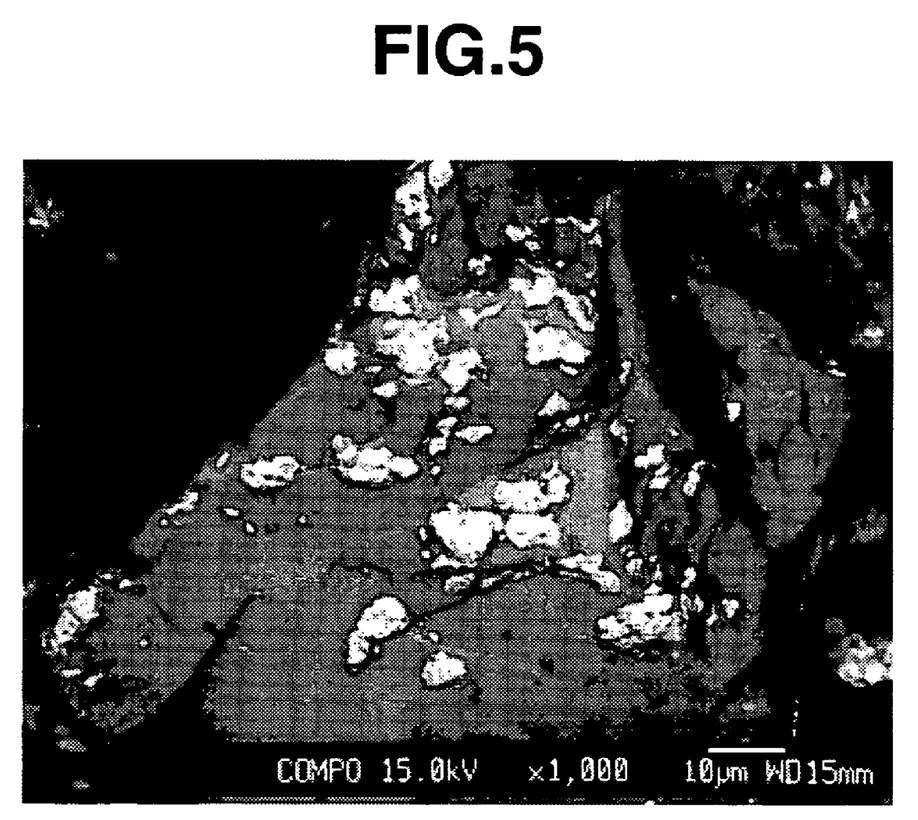
FIG. 5 is a photomicrograph of tin-deposited metallic silicon particles resulting from mechanofusion mixing in Example 7.

100 parts of metallic silicon having an average particle size of 50 μm and 8 parts of tin having an average particle size of 5 μm were mixed. Using a mechanofusion device AM-15F, the mixture was rubbed for one hour in a nitrogen stream under conditions: agitating power 1.5 kW, and casing revolution 1,200 rpm. A back-scattered electron image of the treated particles was taken under a scanning electron microscope. The photomicrograph is shown in FIG. 5. Since heavier elements are reflected lighter in the back-scattered electron image, it is seen from FIG. 5 that tin-containing particles are dispersed and deposited as fines on the surface of metallic silicon.

The mixture prepared above was fed into a fluidized bed reactor equipped with a stirrer through which nitrogen flowed. The reactor was heated to an interior temperature of 480° C. The nitrogen flow was then interrupted, and instead, gaseous chlorobenzene was fed into the fluidized bed at a flow velocity of 2 cm/s. The product gas was condensed in a condenser. Table 5 shows the composition of a sample taken at the steady state of reaction.

Comparative Example 8

100 parts of chemical grade metallic silicon having an average particle size of 50 μm, 6 parts of copper having an average particle size of 75 μm, a catalytic amount of zinc having an average particle size of 75 μm and a catalytic amount of tin having an average particle size of 75 μm were fed into a fluidized bed reactor equipped with a stirrer through which nitrogen flowed. The reactor was heated to an interior temperature of 480° C. The nitrogen flow was then interrupted, and instead, gaseous chlorobenzene was fed into the fluidized bed at a flow velocity of 2 cm/s. The product gas was condensed in a condenser. Table 5 shows the composition of a sample taken at the steady state of reaction.

TABLE 5

| | | | | (unit: weight %) | | |
|---|---|---|---|---|---|---|
| | Catalyst | Diphenyl-dichlorosilane | Phenyl-trichlorosilane | Biphenyl | Benzene | Unreacted gas |
| Example 6 | Sn | 22.7 | 8.0 | 0.2 | 2.8 | balance |
| Comparative Example 7 | Sn | 36.0 | 8.3 | 0.2 | 2.7 | balance |
| Comparative Example 8 | Cu + Zn + Sn | 24.0 | 14.7 | 2.1 | 6.8 | balance |

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A process of preparing organohalosilanes having the general formula (I):

$$R_nH_mSiX_{(4-n-m)} \qquad (I)$$

wherein R is a monovalent hydrocarbon group, X is a halogen atom, n is an integer of 1 to 3, m is an integer of 0 or 1, and the sum of n+m is 1 to 3, said method comprising
charging a reactor with a contact mass comprising metallic silicon and a catalyst and
feeding an organohalide-containing gas to the reactor,
wherein the catalyst comprises 0.01 to 50 parts by weight (calculated as metallic tin) of tin or a tin compound as an active component per 100 parts by weight of the metallic silicon and 0 to 20 parts by weight of a co-catalyst selected from zinc, antimony, arsenic, and phosphorus and compounds and alloys thereof per 100 parts by weight of the metallic silicon,
with the proviso that the amount of the co-catalyst is smaller than the amount of tin, and
with the proviso that copper is included as an incidental impurity in the metallic silicon and the catalyst in an amount of 0 to less than 0.1% by weight based on the metallic silicon.

2. The process of claim 1, wherein the tin or tin compound is in the form of metallic tin, tin alloy, tin oxide or tin halide.

3. The process of claim 1, wherein metallic silicon and the tin or tin compound are previously mixed under substantial shear forces or heat treated to form a precursor, prior to the charging step.

4. The process of claim 1, wherein metallic silicon particles and the tin or tin compound are rubbed together by mechanically applying high shear forces in a non-oxidizing atmosphere, for dispersing and depositing the tin or tin compound onto surfaces of metallic silicon particles, prior to the charging step.

5. The process of claim 4, wherein means for mechanically applying high shear forces is a mechanofusion device, ball mill, media agitating mill, planetary mill, high-speed tumbling mill, jet mill, shearing mill or roller mill.

6. The process of claim 4, wherein the non-oxidizing atmosphere comprises nitrogen, argon, hydrogen or a mixture thereof.

7. The process of claim 1, wherein the organohalide is phenyl chloride whereby phenylchlorosilanes are prepared.

8. The process of claim 1, wherein copper is present in an amount of 0 to 0.05% by weight based on the metallic silicon.

9. The process of claim 1, wherein tin or tin compound is present in an amount of 1 to 50 parts by weight per 100 parts by weight of the metallic silicon.

10. The process of claim 7, wherein the organohalosilanes of formula (I) comprise diphenyldichlorosilane.

11. The process of claim 1, wherein the metallic tin or tin compound arc powders having an average particle size in the range of 1 to 200 μm.

12. The process of claim 1, wherein the metallic tin or tin compound are powders having an average particle size in the range of 1 to 30 μm.

* * * * *